United States Patent [19]

Hymanson et al.

[11] Patent Number: 4,586,900
[45] Date of Patent: May 6, 1986

[54] DENTAL ASPIRATOR TUBE

[76] Inventors: Victor Hymanson, 37 Knowsley St., Bury, Lancashire; Julian E. Paul, 94 Moss La., Sale, Manchester M33 5BT, both of England

[21] Appl. No.: 710,848

[22] Filed: Mar. 12, 1985

[51] Int. Cl.[4] ............................................. A61C 17/09
[52] U.S. Cl. ....................................................... 433/96
[58] Field of Search ..................................... 433/91, 96

[56] References Cited

U.S. PATENT DOCUMENTS 1,722,676  7/1929  Parker ................................... 285/177
3,460,255  8/1969  Hutson ................................... 433/91
4,083,115  4/1978  McKolvey ............................. 433/96

Primary Examiner—Robert Peshock
Attorney, Agent, or Firm—Pearson & Pearson

[57] ABSTRACT

A dental aspirator tube comprises a tubular handle having a tip at one end for insertion into a patient's mouth and which is adapted to be connected at its other end via a length of flexible tubing to suction equipment. The tip is formed by a bent tube which is securely fixed to the tubular handle. The flexible tubing is detachably connected to the handle via a tapered or graduated connector section. The tip handle and connector are preferably formed as an integral plastics structure.

3 Claims, 1 Drawing Figure

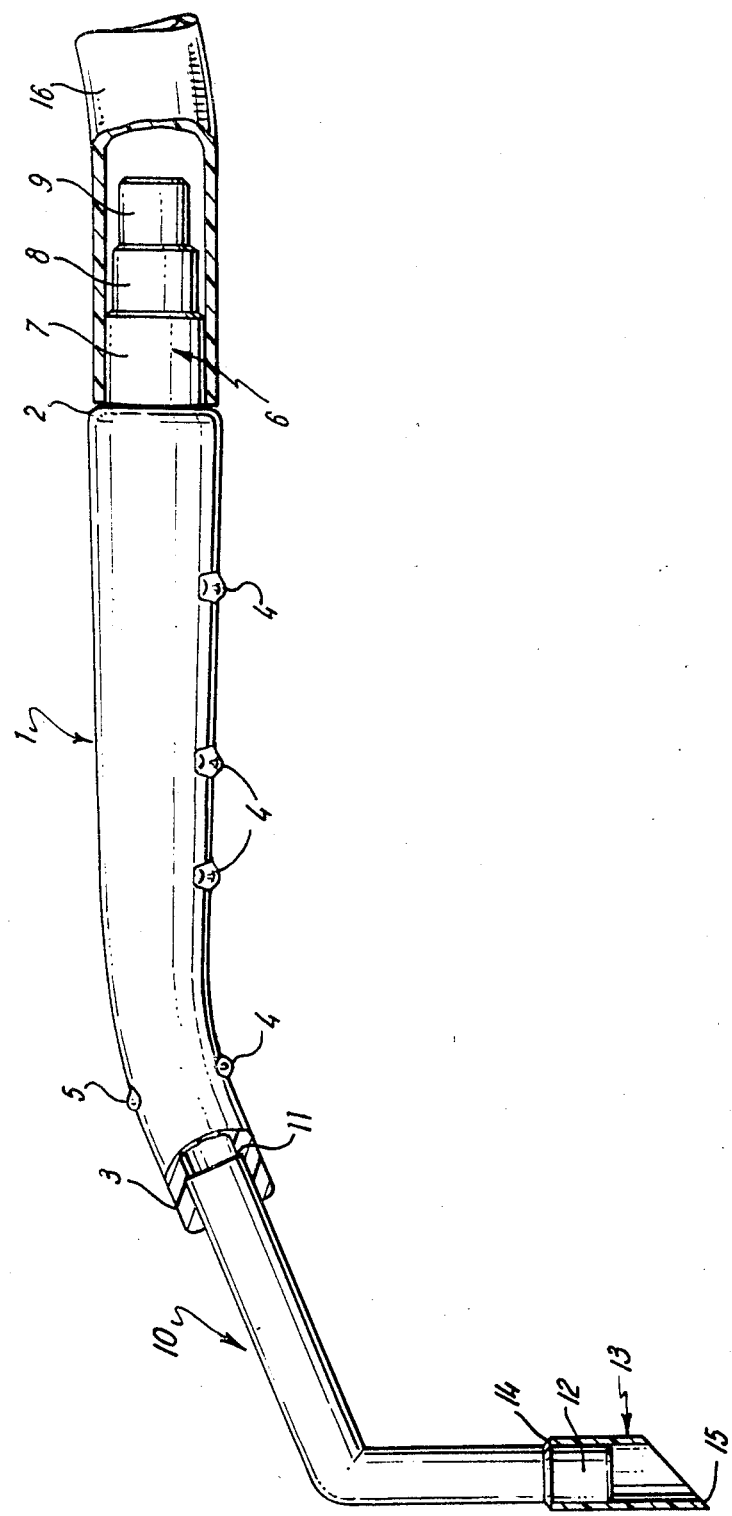

DENTAL ASPIRATOR TUBE

This invention relates to a dental aspirator tube by which is meant a hand-held tube having a tip at one end for insertion into a patient's mouth and which is adpated to be connected at its other end to a source of suction. Such aspirator tubes are used to remove liquid and debris from the patient's mouth and often also for manipulative purposes, particularly to retract soft tissue away from the patient's teeth or gums.

One known form of dental aspirator tube is formed from metal and has a tubular handle which can be held in the palm of the hand. At one end, the handle is permanently connected to the suction source via a length of flexible tubing. At its other end, a tip is in the form of a short aluminium tube which is bent through a right angle is inserted into the handle and retained in position by frictional engagement with an O-ring.

This known aspirator tube is particularly convenient to use but has the disadvantage that the O-ring tends to wear and the tip becomes loose with time. Permanent fixing of the tip in the handle is not acceptable since it is necessary to allow for removal for sterilisation and also periodic replacement. A further disadvantage is that the aspirator tube forms an integral part with the suction source (and associated equipment) and cannot therefore be used with other suction equipment.

An object of the present invention is to provide a dental aspirator tube with which the abovementioned disadvantages do not arise or at least are minimised.

According to the invention therefore there is provided a dental aspirator tube having a tubular handle, a tip securely fixed to one end of said handle and terminating in a narrow tubular end portion for insertion into a patient's mouth, and, at the opposite end of said handle, a tubular connector section adapted to be releasably connected to suction tubing.

With this arrangement it will be appreciated that the aspirator tube, being formed as a separate instrument, can be used with different suction equipment by appropriate connection thereto. Moreover, the aspirator tube and holder can be sterilised and replaced as required in its entirety whereby problems due to looseness between the tip and the handle need not arise.

Having regard to the ease with which the entire aspirator tube can be replaced, relatively inexpensive materials may be used. Preferably therefore the aspirator tube is formed as one or more plastics mouldings. In this case a suitable plastics material capable of being sterilised in wet or dry sterilisers up to a temperature of 200° C. is preferably used.

With regard to the tip, this preferably constitutes a tube which is bent through an angle which may be equal or close to 90°. Such tube is preferably of smaller diameter than the handle and may be substantially of a common diameter throughout. The terminal end portion may be provided with a short, protective end tube, e.g. formed from flexible polyvinylchloride plastics material, and this may have a bevelled end and may be rotatable so that the disposition of the bevel can be adjusted.

The tip may be permanently attached to the handle. For example the tip may be integrally moulded in one piece with the handle, or the tip may be formed separately and bonded to the handle.

With regard to the said connector section, this may also be integrally moulded in one piece with the handle or bonded thereto or fitted tightly therein. Most preferably the connector section is tapered or graduated so as to fit tubing of different diameters.

The handle is preferably shaped to fit comfortably in the plam of the hand. Thus, the handle may comprise a tube which tapers slightly and also is curved or bent slightly towards the tip. Finger grips or guides may be provided at appropriate positions on the tube.

The invention will now be described further by way of example only and with reference to the accompanying drawing which is a diagrammatic side view partially sectioned of one form of an aspirator tube according to the invention.

The aspirator tube comprises a tubular handle having a one-piece moulded plastics control body portion 1 adapted to fit comfortably in the palm of the hand. This body portion 1 is of circular cross-section and tapers from a first end 2 to a second end 3. Also, the body portion 1 is curved or angled downwardly adjacent the second end 3. Four small, smooth projections 4 are provided at longitudinally spaced positions along the bottom of the body portion 1, and a single such projection 5 is provided at the top.

At the first end 2 of the body portion 1 there is fixed a one-piece circular cross-section plastics connector tube 6 disposed coaxially relative to the portion 1 and having three parts 7, 8, 9 of progressively decreasing diameter. The connector 6 may be tightly inserted within and bonded relative to the first end 2.

At the second end 3 of the body portion 1 there is fixed a one-piece plastics tube 10 having a first and second end and a uniform circular cross-section throughout its length. The tube 10 is bent through an angle as shown. The tube 10 is inserted tightly into the second end 3 of the portion 1 up to an internal abutment or shoulder 11 and may be bonded in position or otherwise permanently or semi-permanently retained in position so that it is normally incapable of movement relative to the portion 1. The terminal end portion 12 of the tube is provided with a removable flexible vinyl end tube 13 which engages a raised rim 14 around the end portion 12 and has a bevelled end 15. The tube 13 fits securely on the end portion 12 but can be readily rotated to adjust the disposition of the bevel 15.

In use, the aspirator tube is connected to a free-standing dental suction unit via flexible plastics tubing 16 which fits securely yet removably over the connector 6 having a first and second end. It will be appreciated that different diameters of tubing can be accommodated. The handle is then held in the hand and the end portion 12 with the vinyl end tube 13 inserted into the patient's mouth. The projections 4, 5 act as finger grips or guides. The aspirator tube comprises an integral plastics structure which is simple and inexpensive to manufacture and convenient to use. It can be detached from the tubing 16 for sterilisation using conventional sterilisation equipment and it can be discarded and replaced when required.

It is of course to be understood that the invention is not intended to be restricted to the details of the above embodiment which are described by way of example only.

We claim:
1. A dental aspirator tube comprising:
an elongated tubular plastics handle having first and second ends and which is tapered from said first end towards said second end thereof, a major portion of the handle starting from said first end being straight and the remaining minor portion up to said second end being inclined at an angle to said major portion, and said handle being shaped to define integral finger grips thereon;

a plastics tip for insertion into a patient's mouth comprising a tube which is of a uniform diameter throughout which diameter is smaller than that of second end of said handle, said tube having first and second ends and being straight except for a bend therein through a sharp angle at a position intermediate said ends, said tube being securely fixed at the said first end thereof in the said second end of said handle;

a short tubular end protector mounted on said second end of said tip tube so as to project freely therefrom, said protector terminating in a bevelled free end;

a tubular plastics connector section having first and second ends, said first end thereof having a diameter which is smaller than that of the said first end of the handle, said first end of the connector section being securely fixed in the first end of the handle, and said section having successive portions of progressively reduced diameter from said first end to said second end thereof so as to be capable of fitting securely yet releasably within suction tubing of different diameters.

2. A dental aspirator tube according to claim 1, wherein said short tubular end protector is detachably mounted on said second end of said tip tube and is rotatably adjustable relative thereto.

3. A dental aspirator tube according to claim 1, wherein said tip tube is permanently fixed to the handle.

* * * * *